US 8,374,887 B1

(12) United States Patent
Alexander (10) Patent No.: US 8,374,887 B1
(45) Date of Patent: Feb. 12, 2013

(54) SYSTEM AND METHOD FOR REMOTELY SUPERVISING AND VERIFYING PHARMACY FUNCTIONS

(76) Inventor: Emily H. Alexander, Alpine, TX (US)

(*) Notice: Subject to any disclaimer, the term of this patent is extended or adjusted under 35 U.S.C. 154(b) by 1731 days.

(21) Appl. No.: 11/056,511

(22) Filed: Feb. 11, 2005

(51) Int. Cl.
*G06Q 50/00* (2012.01)
(52) U.S. Cl. ............... 705/2; 705/3; 700/216; 700/237; 700/244
(58) Field of Classification Search .......... 705/2–4; 700/241, 216, 237, 244
See application file for complete search history.

(56) References Cited

U.S. PATENT DOCUMENTS

| | | | |
|---|---|---|---|
| 5,713,485 A | 2/1998 | Liff et al. | |
| 5,797,515 A | 8/1998 | Liff et al. | |
| 5,907,493 A | 5/1999 | Boyer et al. | |
| 6,330,491 B1 | 12/2001 | Lion | |
| 6,438,451 B1 | 8/2002 | Lion | |
| 6,711,460 B1 | 3/2004 | Reese | |
| 6,814,255 B2 | 11/2004 | Liff et al. | |
| 7,006,893 B2 | 2/2006 | Hart et al. | |
| 2002/0100762 A1 | 8/2002 | Liff et al. | |
| 2003/0050731 A1* | 3/2003 | Rosenblum | 700/232 |
| 2004/0172289 A1 | 9/2004 | Kozic et al. | |
| 2004/0204954 A1 | 10/2004 | Lacko | |

OTHER PUBLICATIONS

Sandra C. Woodall, Pharm.D., "Remote Order Entry and Video Verification," Aug. 2004, Joint Commission on Accrditation of Healthcare Organizations, vol. 30 No. 8, 442-447.*
Yahoo Mail, Oct. 1, 2002.*
CardinalCSC After hours pharmacy service, 2003.*
Canadian Pharmacists Association, Environmental Scan of Pharmacy Technicians, Sep. 2001.*
Joseph Tracy, "A Guide to Getting Started in Telemedicine," Telemedicine Technical Assistance Documents, Chapter 10, 2004, pp. 206-240.
"Regulatory Compliance News Summary; now includes global pharmaceutical regulatory news," Aug. 24, 2004, Regulatory Compliance News Summary from First Consulting Group, 7 pages.

* cited by examiner

*Primary Examiner* — Sind Phongsvirajati
(74) *Attorney, Agent, or Firm* — Robert C. Kowert; Meyertons, Hood, Kivlin, Kowert & Goetzel, P.C.

(57) ABSTRACT

A system and method for remotely supervising and verifying pharmacy functions performed by a non-pharmacist at an institutional pharmacy. The institutional pharmacy and a remotely located pharmacist are linked via wired and/or wireless telecommunication systems in a manner that enables the pharmacist to remotely supervise and verify the correct performance of pharmacy functions by non-pharmacist personnel. Images of the pharmacy work performed may be captured using any of a number of types image capture devices. Captured images and corresponding documentation may be transmitted from institutional pharmacy to the remotely located pharmacist, either directly or via a web site accessible to both. After verifying that the pharmacy work was correctly performed, the remote pharmacist may provide the institutional pharmacy with an initialed copy the captured image(s), or other documentation, indicating such verification. Receiving the pharmacist's verification may authorize the non-pharmacist to further process the work.

27 Claims, 9 Drawing Sheets

SYSTEM AND METHOD FOR REMOTELY SUPERVISING AND VERIFYING PHARMACY FUNCTIONS

BACKGROUND OF THE INVENTION

1. Field of the Invention

The present disclosure relates to pharmacy services, and more specifically, to a method and a system for remotely supervising and verifying technical pharmacy functions performed by a non-pharmacist located in an institutional pharmacy

2. Description of the Related Art

A pharmacist's scope of practice in institutions, such as hospitals or correctional facilities, includes preparing, packaging, compounding, and labeling medication, compounding sterile products, as well as other medication related activities. Many technical functions involving the preparation and distribution of drugs may be performed in the pharmacy by non-pharmacist personnel, usually a pharmacy technician or licensed nurse. When a non-pharmacist performs such functions a pharmacist must generally verify their work.

When a non-pharmacist performs technical pharmacy functions, such as pursuant to a written medication order, a pharmacist typically verifies the work, in part, by comparing it to either a copy of the original medication order, or a medication order previously entered into the patient's medication profile. The pharmacist also supervises the work of the non-pharmacist, and verifies that the medication product has been correctly and accurately prepared, labeled, compounded, and/or packaged. When a non-pharmacist performs technical pharmacy functions involving prepackaging, labeling, bulk compounding, or batch preparation of medications that will serve as stock medication in the pharmacy department, a pharmacist must generally verify the work in much the same manner. The pharmacist must supervise the work of the non-pharmacist to verify that the medication has been correctly and accurately prepared, labeled, compounded, and/or packaged.

The majority of institutional pharmacies do not have pharmacists on duty 24 hours, 7 day per week, yet patients frequently require medications that are only available in the pharmacy department of an institution when no pharmacist is on duty. Under such circumstances, no pharmacist can supervise or verify the performance of the pharmacy functions performed. As a result, patients may receive medication that has been prepared, packaged, compounded, and labeled without being first verified by a pharmacist. In some cases, a pharmacist on duty later may retrospectively verify that the pharmacy work was performed correctly. For example, when it is necessary that a patient receive a new order for a medication that is only available from the pharmacy after regular pharmacy hours, a nurse, or other non-pharmacist personnel, may enter the pharmacy to obtain the medication for the patient. The patient will have already received the medication by the time a pharmacist returns to duty. Upon the pharmacist's return, he must verify that the nurse used the correct medication, in the correct dose and dosage form, as well as verify documentation regarding the patient for whom the medication was removed, the person removing the medication, and when the removal occurred. An error may thus be discovered, but not prevented by the pharmacist.

Another example of sub-optimal medication safety that may result from lack of pharmacist availability is demonstrated when medication is removed from the pharmacy after hours in a multi-dose packaging form. While this practice increases the potential for medication errors, the lack of pharmacist availability may necessitate it, as follows. If a multi-dose stock bottle of medication was purchased and received in the pharmacy when a pharmacist is not on duty, the unit dose packaging process must wait for the pharmacist's supervision and verification. In this case, if a patient requires this same medication before a pharmacist is on duty, regulations may require that the entire stock bottle be removed from the pharmacy in order for the patient to receive a dose.

SUMMARY

A system and method are described herein for providing certain pharmacy services to institutionalized patients at an institution where a live pharmacist is not available. The institutional pharmacy and a remotely located pharmacist are linked via wired or wireless telecommunication systems in a manner that enables the pharmacist to remotely supervise and verify that pharmacy functions are properly performed by non-pharmacist personnel. In order to facilitate remote supervision and verification, the pharmacist site(s), institutional pharmacy site(s), and a system website may be linked to one another via an Internet connection, virtual private network, or in general any wired or wireless link, so that information may be exchanged. For example, a pharmacist site and an institutional pharmacy site may be linked via an Internet connection, using telephone lines, wireless links, or a combination of wireless links and wired links. Additionally, the pharmacist site and the institutional pharmacy site may be linked to a system website via an Internet connection.

A pharmacist site may include a workstation with one or more monitors, Internet connectivity, printer, scanner, copier, telephone and facsimile machine, according to one embodiment. It may also include a local area network and additional workstations. An institutional pharmacy site may generally include an image capture device (e.g. a visual presenter or document viewer) linked to a workstation, which may be linked to a local area network. The local area network or workstation may be generally linked via an Internet connection, telephone lines, wireless links, or a combination of wireless links and wired links to other sites (e.g. a pharmacist site). The site typically also includes telephone lines, facsimile machine(s), and a printer.

The method and system for remotely supervising and verifying pharmacy functions may include using a image capture device located in the institutional pharmacy, linked to a computer system, to capture images of work performed by non-pharmacist personnel. The image(s) and corresponding documentation are transmitted from the institutional pharmacy to a remotely located computer system, where a pharmacist supervises and verifies the work, and subsequently authorizes non-pharmacist personnel to further process the work.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

Figure 1:
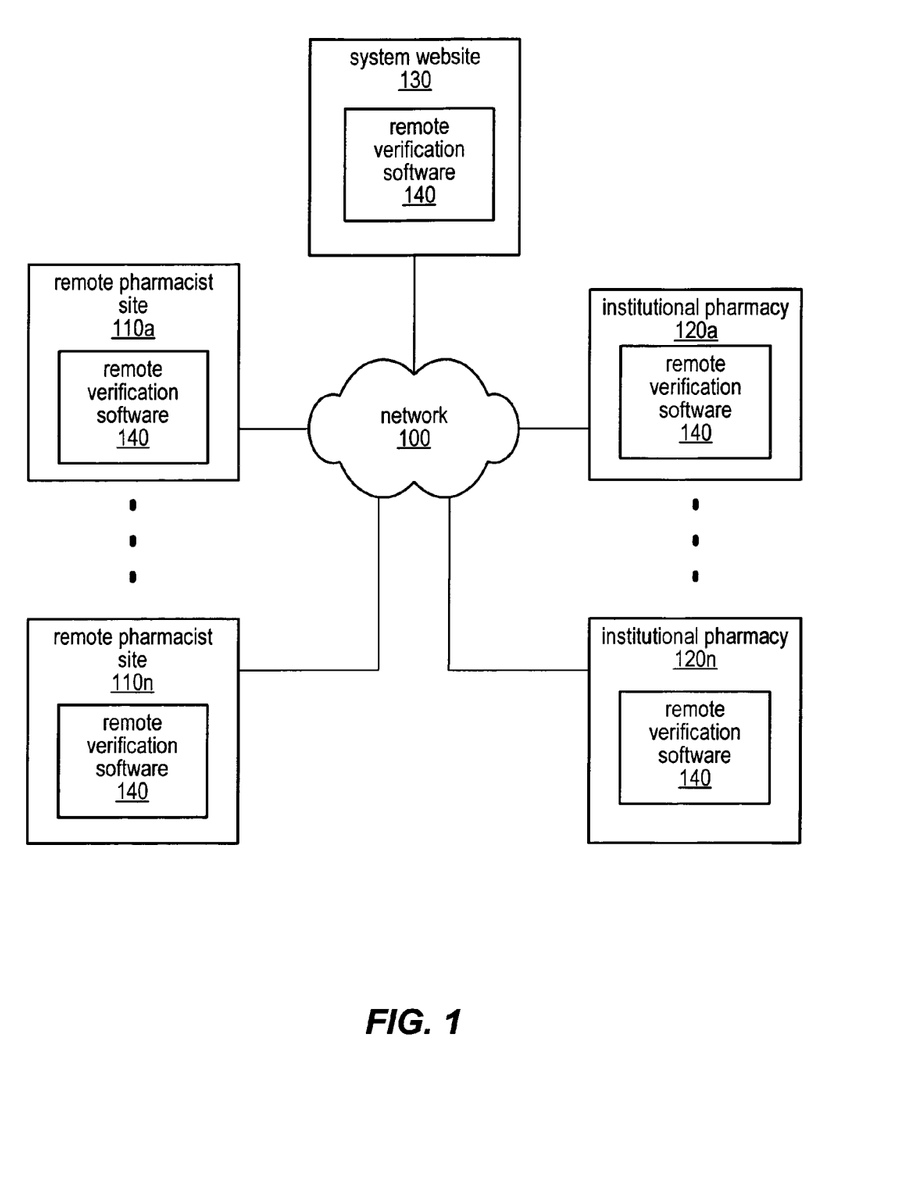
FIG. 1 illustrates, according to one embodiment, a block diagram of a networked environment suitable for implementing remote supervision and verification of pharmacy functions, as described herein.

Pharmacy functions performed by a non-pharmacist may be remotely supervised and verified by a remote pharmacist using a networked environment, such as illustrated by FIG. 1, according to some embodiments. Pharmacists at one or more remote pharmacist sites 110 may remotely supervise and verify pharmacy work tasks performed by non-pharmacists at one or more institutional pharmacies 120, according to some embodiments. Remotely supervised and verified pharmacy work tasks may include pharmacy functions performed pursuant to medication orders and may also include pharmacy functions not related to specific medication orders, according to various embodiments. In general, the term "pharmacy work task" as used herein may describe any pharmacy functions capable of being remotely supervised and verified by the methods and systems described herein, whether or not performed pursuant to a medication order.

As illustrated in FIG. 1, a remote pharmacist site may be communicably linked to one or more institutional pharmacies while located remotely from the institutional pharmacies. For instance, institutional pharmacy 120 and remote pharmacist site 110 may be located in different parts of the same building, in one embodiment. In other embodiments, however, institutional pharmacy 120 and remote pharmacist site 110 may be in different buildings of the same institution, in the same town, in different cities, counties, or states. In general, remote pharmacist site 110 and institutional pharmacy 120 may be located anywhere as long they can communicate with each other either directly or indirectly.

Remote pharmacist site 110 and institutional pharmacy 120 may communicate via any of various wired or wireless communication systems, according to various embodiments. For example, in one embodiment, they may communicate via email over the Internet. In another embodiment, they may communicate via a custom communication protocol configured for exchanging messages related to remotely supervising and verifying pharmacy functions, such as may be implemented by remote verification software 140, as will be discussed herein below. In yet another embodiment, remote pharmacist site 110 and institutional pharmacy 120 may communicate via a website or electronic bulletin board, such as system website 130, by uploading and downloading various documents, images and/or other information related to remotely supervising and verifying pharmacy functions. Additionally, remote pharmacist site 110 may communicate with a pharmacy order entry system or other software at institutional pharmacy 120 via an Internet connection, virtual private network, or any wired or wireless link, according to one embodiment. For example, a pharmacist at remote pharmacist site 110 may communicate with such an order entry system or other software at institutional pharmacy 120 in order to verify a patient's medication order.

As illustrated by FIG. 1, multiple remote pharmacist sites 110 may exist in the system at once, as well as multiple institutional pharmacy sites 120, according to some embodiments. A single remote pharmacist 110 may remotely supervise and verify pharmacy functions performed at more than one institutional pharmacy sites 120. Additionally, a pool of remote pharmacist sites 110 may work together to remotely supervise and verify pharmacy functions performed at multiple institutional pharmacy sites 120, in some embodiments. For example, a number of remote pharmacist sites 110 may each remotely supervise and verify pharmacy functions for any of a number of institutional pharmacy sites 120 on a rotational or as needed basis. For instance, in one embodiment, a pharmacist at remote pharmacist site 110 may check and/or verify images from one or more institutional pharmacy sites 120 randomly chosen out of a number of available institutional pharmacy sites 120. In another embodiment, a remote pharmacist site may remotely verify pharmacy functions performed at a number of institutional pharmacy sites on a first-come first-served basis in which the institutional pharmacies are serviced in the order they notified the remote pharmacist that images were available for verification.

According to some embodiments, pharmacy functions performed at institutional pharmacy 120 that may be remotely supervised and verified may include, but are not limited to:

1. Packaging, prepackaging and labeling unit and multiple dose packages.
2. Medication preparation, packaging, compounding or labeling pursuant to medication orders.
3. Compounding of sterile pharmaceuticals pursuant to medication orders.
4. Bulk compounding or batch preparation.

The terms prepackaging and packaging, as used herein, may refer to two different pharmacy functions. Prepackaging refers to the re-packaging and/or re-labeling quantities of drug products from a manufacturer's original commercial container, such as into a prescription container for dispensing. Packaging, on the other hand, refers to collecting one or more medications into a final package to be dispensed to the ultimate consumer. For example, packaging may refer to a technician selecting appropriate quantities of manufacturer's unit dosed products and/or prepackaged stocked medications necessary to fill a patient's admission orders. The technician may then package the selected medications into a bag with an affixed label indicating the patient for whom the medications were ordered. As with other pharmacy functions, the prepackaging and the final packaging of medications may be remotely supervised and verified by a pharmacist, as described herein.

Remote verification of pharmacy functions performed by non-pharmacists may additionally include, in some embodiments, one or more legally required in-progress checks. In general, remote pharmacist verification of pharmacy work performed by non-pharmacists may include supervision and/or verification of the pharmacy work in various stages of completion as well as verification of any and/or all results of the pharmacy work, according to various embodiments.

The Institutional Pharmacy Site:

An institutional pharmacy 120 may be a pharmacy located in an institution, such as a hospital or correctional facility. In general, institutional pharmacy 120 may be any pharmacy that cannot or does not have a pharmacist on site at all times. As illustrated in FIG. 1, an institutional pharmacy 120 may be linked to a system website 130 and/or one or more remote pharmacist site(s) 110 via any of a number of ways, such as over the Internet, a virtual private network, or, in general, any wired or wireless communication system configured to allow the exchange of information related to remote supervision and verification of pharmacy functions, as described herein. For instance, institutional pharmacy 120 may communicate with remote pharmacist site 110 over network 100, which may be the Internet in one embodiment. In other embodiments, institutional pharmacy 120 may communicate with remote pharmacist site 110 directly over a telecommunications system, such as the Public Switched Telephone Network (PSTN) or over a cellular or satellite telecommunications system.

In some embodiments, system website 130 may represent an electronic bulletin board, or other shared electronic data storage facility, to which images, documents, and/or other files may be posted, uploaded, or otherwise stored. Images uploaded or posted to a web site or bulletin board may be compressed, encrypted, or combined (either compressed or uncompressed) into a single file, according to various embodiments. For example, in one embodiment, captured images may be uploaded in an encrypted form and a key or password to decrypt the images may be provided to a remote pharmacist in a separate communication. Furthermore, system website 130 may require secure login credentials, such as a username and password, before allowing images to be uploaded or accessed. Alternatively, a public/private key encryption schema may be utilized to ensure the security of the captured images in some embodiments. For example, the captured images may be encrypted using the remote pharmacist's public encryption key and may be decrypted by the pharmacist using the pharmacist's private encryption key. Additionally, any of various forms of secure electronic communication may be utilized to transfer the captured images in some embodiments. For example, in one embodiment, one or more images of pharmacy work may be transferred to system website 130 via a secure http protocol, such as HTTPS. In yet other embodiments, captured images may be digitally signed using digital certificate technology. For instance, the images may be digitally signed using the institutional pharmacy's digital signature or certification which a remote pharmacist may verify using an appropriate digital certification authentication authority. As encryption, secure electronic communication, and digital signature and certificate technologies are well understood in the art, they are not discussed in detail herein.

Figure 2:
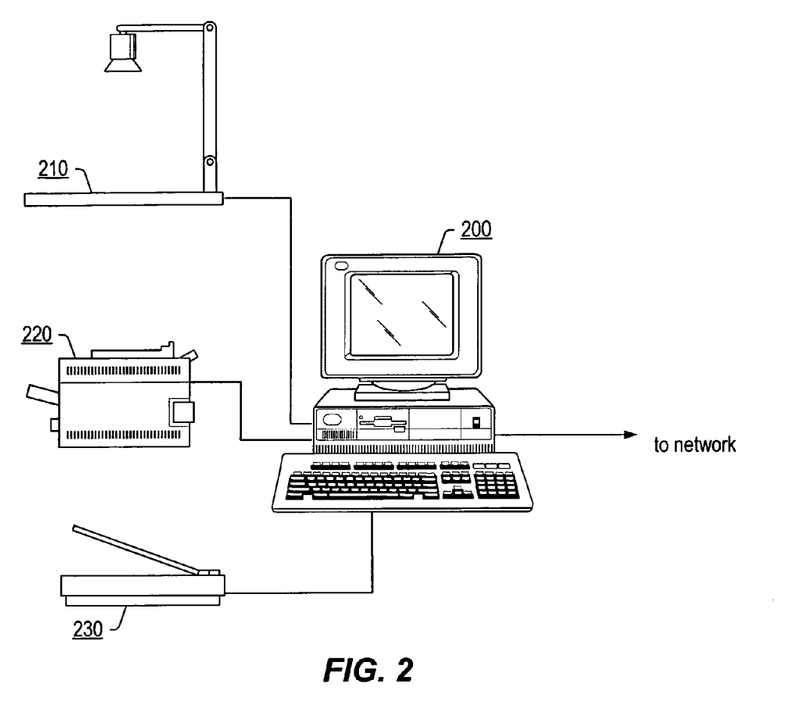
FIG. 2 illustrates one embodiment of an exemplary institutional pharmacy workstation.

Referring now to FIG. 2, which illustrates one embodiment of an institutional pharmacy workstation for implementing remote supervision and verification of pharmacy functions, as described herein. One or more workstations, such as illustrated in FIG. 2 may be located at institutional pharmacy 120, according to some embodiments. As illustrated by FIG. 2, such a workstation may include an image capture device capable of accommodating three-dimensional objects, such as image capture device 210, that may be coupled to a computer 200. An institutional pharmacy workstation may, in some embodiments, also include a printer 220, scanner 230, and may also have a telephone and a facsimile machine, not shown in FIG. 2.

Image capture device 210 may be any of a number of different types of image capture devices configured to capture still and/or video images or clips, according to various embodiments. For example, in one embodiment, image capture device 210 may be an off-the-shelf digital camera mounted appropriately to capture images of pharmacy work. In another embodiment, image capture device 210 may be a visual presenter, while in other embodiments, image capture device may be a web cam configured to capture still and/or video images or clips. In yet other embodiments, image capture device 210 may be a custom image capture device configured specifically for capturing images of pharmacy functions. The manner of capturing images with image capture device 210 may also vary from embodiment to embodiment. For instance, in one embodiment, image capture device 210 may be mounted above a pharmacy work area, while in other embodiments, image capture device 210 may be mounted proximate to an area specifically for arranging ingredients, materials, and/or documentation for pharmacy functions. In yet other embodiments, image capture device 210 may be a handheld image capture device capable of communicating, either directly or indirectly with computer 200.

When non-pharmacist personnel, such as pharmacy technicians and/or licensed nurses, perform pharmacy functions requiring the supervision and verification of a pharmacist, in the absence of an on-site pharmacist, the still image capture device can be used to capture one or more images of the pharmacy work performed. The captured images may, in some embodiments, include images of all work and documentation required to properly supervise and verify the correct and accurate preparation, labeling, compounding, prepackaging and/or packaging, of any pharmacy work performed. The captured images may also include any additional documentation required for record keeping purposes, in some embodiments. Multiple images may be captured for remote supervision and verification process as needed, according to some embodiments. For example, if all documentation and materials required for the pharmacy work do not fit in the view of image capture device 210, two or more images may be captured.

In some embodiments, multiple images may be uploaded together as a single post to a website or bulletin board, such as system website 130. For instance, in one embodiment, multiple images may be uploaded to a website or bulletin board as a single post and inclusion of multiple images in a single post may indicate all of the included images are part of a single pharmacy task that requires remote supervision and verification. Alternatively, in other embodiments, each of the captured images for a single pharmacy work task, whether for a medication order or other pharmacy work, may contain some indication that they are part of the same pharmacy work task. For example, in one embodiment, each related image could include a unique reference number associated with the pharmacy work task. Reference numbers may be included in captured images using a number of different techniques, according to various embodiments. For example, in one embodiment, a small piece of paper with a reference number printed on it may be in the view of image capture device 210 when each image is captured. In another embodiment, reference numbers may be overlayed on, inserted in, or otherwise graphically added to the captured images, such as by software in computer 200. In yet other embodiments, image capture device 210 may be configured to automatically graphically include, add, or overly reference numbers to captured images. An order identification number from a medication order may be included as a reference number in captured images, according to one embodiment. In other embodiments, reference numbers may be generated for each set of related images, such as by an order entry system for entering medication information into a patient's medication profile. In general, any type or sort of reference indicators, either alphanumeric or graphical, may be used to indicate related captured images.

Figure 3:
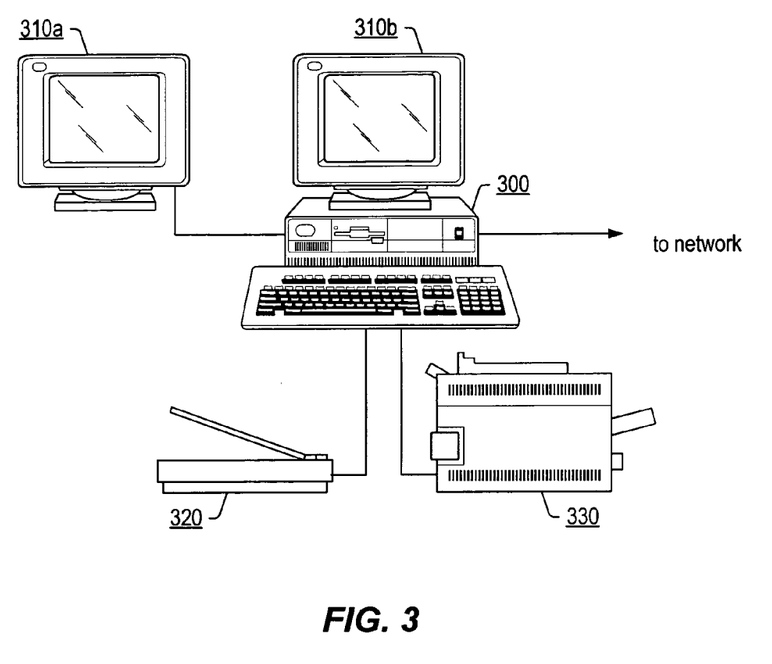
FIG. 3 illustrates one embodiment of an exemplary remote pharmacist workstation.

The Remote Pharmacist Site:

FIG. 3 illustrates an exemplary workstation used by a pharmacist at remote pharmacist site 110, according to some embodiments. A remote pharmacist workstation may include a computer 300 with one or more monitors, such as monitors 310*a* and 310*b*, allowing viewing captured images of pharmacy work performed as institutional pharmacy 120. According to some embodiments, a remote pharmacist workstation may include two monitors 310 coupled to computer 300 to allow simultaneous viewing of two images. A remote pharmacist workstation 110 may also have Internet connectivity for communicating with institutional pharmacy 120, according to one embodiment. A remote pharmacist workstation 110 may, in some embodiments, also include, but is not limited to, a scanner 320, a printer 330, telephone, fax machine, and/or a copier. A remote pharmacist workstation may communicate with one or more institutional pharmacies 120 and/or with system website 130 via an Internet connection, virtual private network, LAN, WAN, or in general any wired or wireless link, according to various embodiments.

In some embodiments, more than one pharmacist may be on duty at a single remote pharmacist site 110 and thus a remote pharmacist site 110 may include more than one remote pharmacist workstation. In such an embodiment, multiple remote pharmacist workstations may be linked via a local network, such as a LAN or WAN, and each workstation may be configured to communicate via an Internet connection provided by the local network.

Each remote pharmacist site 110 may have one or more pharmacist on duty, as well as other non-pharmacist support personnel, according to various embodiments. Any pharmacist that remotely supervises and/or verifies pharmacy functions performed by non-pharmacist personnel at institutional pharmacy 120 from a remote pharmacist site 110 may be required to have licensure to practice pharmacy in the state in which the institutional pharmacy 120 being serviced is located, in accordance with state laws. As noted above, a pharmacy functions performed at institutional pharmacy 120 may be remotely supervised and verified by a pharmacist at a remote pharmacist site remotely located from institutional pharmacies 120, according to various embodiments. In general a remote pharmacist site 110 may be in any location, including another pharmacy, but generally would not be located in the same facility as the institutional pharmacy it is serving. Although, in certain embodiments, a pharmacist located in one part of a large institution may remotely supervise and verify pharmacy functions performed in multiple institutional pharmacies 120 located in other parts of the same institution. For example, a large institution may include one or more different pharmacy stock areas, or satellite pharmacies, that operate under a single pharmacy license and in some embodiments pharmacy functions performed at satellite pharmacies may be remotely supervised and verified by a remote pharmacist either on duty in a main pharmacy, a different one of the satellite pharmacies, or located offsite. Alternatively, in other embodiments, a large institution may include more than one pharmacy and pharmacy functions performed at one pharmacy may be remotely supervised and verified by a pharmacist at a different one of the pharmacies.

A remote pharmacist site 110 may even change physical locations over time, according to some embodiments. For example, in one embodiment, a pharmacist working at a remote pharmacist site 110 in Texas may service institutional pharmacies 120 in Utah. Such a pharmacist may leave Texas and travel to another location, perhaps Colorado, and may continue to service the institutional pharmacies in Utah. For instance, the pharmacist may leave Texas after a shift of work there, and may arrive in Colorado before her next scheduled shift with the institutional pharmacies in Utah. Given the portable nature of modern computer equipment, a pharmacist may take a remote pharmacist workstation, such as illustrated in FIG. 3, while traveling between remote pharmacist sites 110, according to one embodiment.

According to some embodiments, a single remote pharmacist site 110 may service more than one institutional pharmacy 120 and a single institutional pharmacy 120 may be served by more than one remote pharmacist site 110. Additionally, more than one pharmacist may work at a remote pharmacist site 110. In general, any pharmacist at any remote pharmacist site 110 may remotely supervise and verify pharmacy work performed at any institutional pharmacy 120, according to some embodiments. For example, institutional pharmacy site 120 may be serviced by one pharmacist at remote pharmacist site 110*a* on Mondays and may be serviced by a different pharmacist, either at the same remote pharmacist site or a different remote pharmacist site, on Tuesdays. On Wednesdays, institutional pharmacy site 120 may be serviced by a pharmacist at remote pharmacist site 110*b*. Additionally, according to one embodiment, institutional pharmacy site 120 may be serviced by two (or more) different remote pharmacist sites at the same time while a single pharmacist at a remote pharmacist site may service two different institutional pharmacies at the same time.

Figure 4:
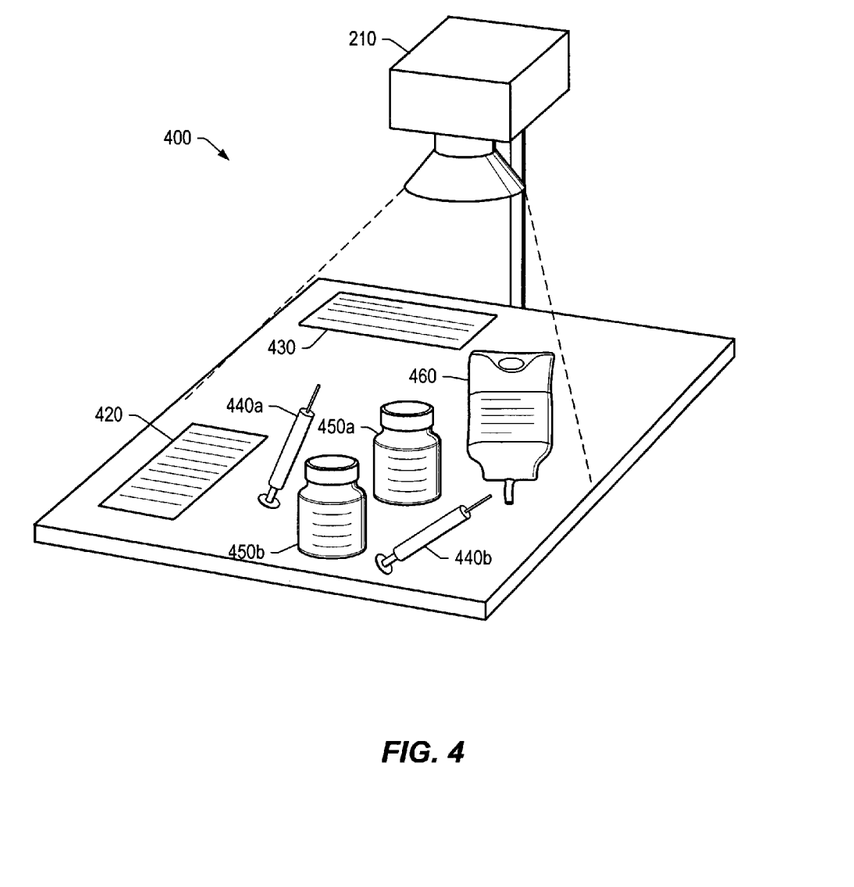
FIG. 4 illustrates an exemplary image capture device suitable for implementing remote supervision and verification of pharmacy functions, in one embodiment.

Turning now to FIG. 4, which illustrates image capture device 210 capturing an image of pharmacy work for remote supervision and verification, according to one embodiment. When a non-pharmacist worker produces pharmacy work, such as pursuant to a medication order or other pharmacy work task, one or more images of the pharmacy functions performed may be captured by image capture device 210. For instance, after performing a pharmacy function requiring supervision and verification by a pharmacist, the non-pharmacist worker may move the job to image capture device 210 and may display all materials and documentation required to properly supervise and verify correct and accurate preparation, labeling, compounding, prepackaging and/or packaging performed during the pharmacy functions, according to one embodiment. For example, in one embodiment, a non-pharmacy worker may perform one or more pharmacy functions and may capture images of the materials used, such as medicine vials 450*a* and 450*b*, syringes 440*a* and 440*b*, intravenous product 460, and documentation 420 and 430, as illustrated in FIG. 4. In some embodiments, several images may be captured as the work is performed, each capturing a different stage of the pharmacy work being performed. Additionally, one or more image may be captured of the completed work. In some embodiments, the worker may move and display the materials and documentation for image capture, while in other embodiments, images may be captured of the materials and documentation in place as they are used during the performance of pharmacy functions.

According to some embodiments, multiple captured images for a single pharmacy work task may be included in a single upload or post to a website or bulletin board, such as to system website 130. Including multiple images in single upload or post may, in certain embodiments, indicate that the images are all related to the same pharmacy work task. Alternatively, in another embodiment, each image may include a reference indicator that links the materials and documentation displayed to a corresponding pharmacy work task, such as a medication order. Such a reference indicator may be an original order, a copy of an original order, or a listing containing a unique medication order number generated from the patient's medication profile, such as a complete label, medication fill list, or a Medication Administration Record, according to various embodiments. The exact nature of such a reference indicator may vary from embodiment to embodiment or within a single embodiment. Additionally, any documentation required by policy or law for the pharmacy work performed may also be included in captured images used for remote supervision and verification. Such documentation may include, but is not limited to, the patient's name, the pharmacy location, the date and time, and/or the full signature and/or title of person performing the pharmacy functions or removing the medication from the pharmacy, according to different embodiments.

In some embodiments, a pharmacist may remotely verify pharmacy work via a real-time collaboration tool. For instance, software may be installed at both an institutional pharmacy site and at a remote pharmacist site allowing a pharmacist to view in real-time, or near real-time, images of the pharmacy work being performed. In one embodiment, a real-time collaboration tool may include software that interfaces with imaging device 210 to allow a non-pharmacist perform pharmacy work at an institutional pharmacy to transmit live images of the pharmacy work being performed. For example, the institutional pharmacy site and the remote pharmacist site may be connected over the Internet via a custom protocol for viewing remote pharmacy work, such as may be implemented by remote verification software 140 illustrated in FIG. 1. Alternatively, in another embodiment, a live feed from a camera capturing pharmacy work being performed may be transmitted to a remote pharmacist using standard, off-the-shelf, video conferencing and/or collaboration software. Thus, in some embodiments, a remote pharmacist may supervise pharmacy work as it is being performed. For example, in one embodiment, a remote pharmacist may verify each step as it is performed and may provide an indication to a non-pharmacist performing the pharmacy that the step was performed correctly. In such an example, the remote pharmacist may provide verification feedback via the same collaboration software, or via another method, such as by telephone.

Figure 5:
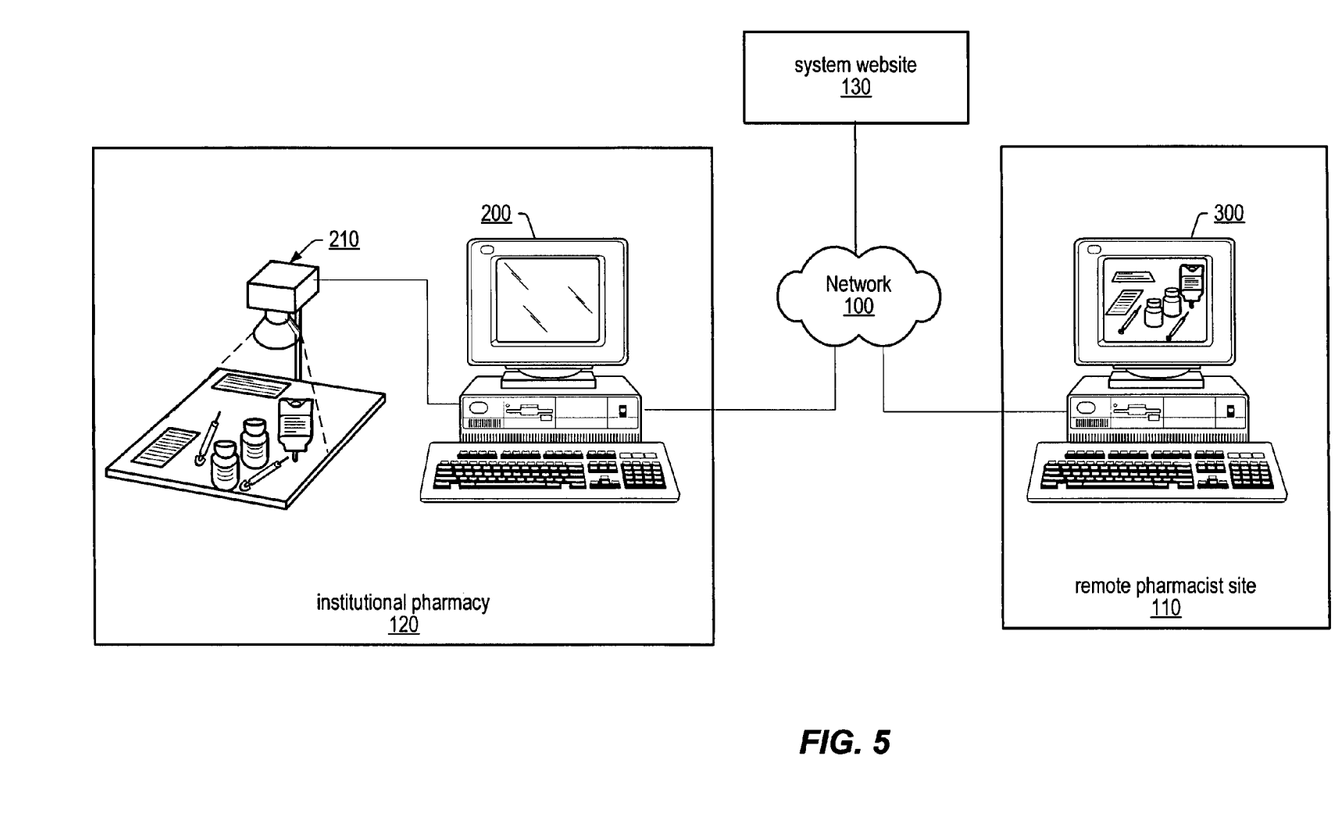
FIG. 5 illustrates an exemplary system for remotely supervising and verifying pharmacy functions, according to one embodiment.

FIG. 5 illustrates an image captured on image capture device 210 at institutional pharmacy 120 being sent and viewed at remote pharmacist site 110, in one embodiment. For example, a nurse, or other non-pharmacy personnel, at institutional pharmacy Site 120 may enter the pharmacy and compound a sterile intravenous product that was ordered for a patient after pharmacy hours and was not available outside of the pharmacy department. A pharmacist may have entered the mediation order into the patient's medication profile and may also have generated a label for the intravenous product via the pharmacy's order entry software. According to one embodiment, after visually inspecting the final product, such as for particulate matter, the nurse may place the labeled sterile intravenous product, with label and base solution content clearly visible, on image capture device 210's display area. Additionally, in one embodiment, one or more of the following items may also be placed on a display area of image capture device 210:

1. A vial of sterile water, with label clearly visible, which was used to reconstitute the medication vial added to the final product.
2. A syringe with the plunger pulled back to the marking on the syringe that indicates the volume of sterile water used to reconstitute the medication vial.
3. The vial of medication that was reconstituted, with label clearly visible, a portion of which was added to the final product's base solution.
4. A syringe with the plunger pulled back to the marking on the syringe that indicates the volume of reconstituted medication that was added to the base solution to prepare the final product.

If all the items listed above do not reasonably fit on the display area, the nurse may, in some embodiments, capture additional images that contain any items necessary to check the work performed. Additional items not listed above may also be included in captured images, such as a document with the current date and/or time, her full signature, and title, according to one embodiment.

The captured image(s) may be transmitted to system website 130 via a network or telecommunication link, according to one embodiment. Image capture device 210 may be coupled to computer 200 which itself may be coupled to network 100. In one embodiment network 100 may represent a local area network providing a connection to the Internet, while in other embodiments, network 100 may represent the Internet to which computer 200 may connect directly. The non-pharmacist worker may log onto system website 130 to upload the captured image(s), in one embodiment. The captured image(s) may be transmitted from the workstation at institutional pharmacy 120 to system website 130 and may be downloaded by a workstation at remote pharmacist site 110, according to some embodiments. In other embodiments, however, captured images may be directly transmitted to remote pharmacist site 110, via email for example. A pharmacist at remote pharmacist site 110 may view the pharmacy work performed at institutional pharmacy 120, as well as any other information necessary to conduct process checks and verify that the medication in the captured image(s) was correctly and accurately prepared, labeled, compounded, and/or packaged. Examples of information that may be included in captured images to allow supervision and verification of pharmacy work and medication removal may include, but are not limited to the following:

1. Medication labels, solution labels, final product labels.
2. Supplies used in compounding the product.
3. Equipment indicating volumes used in product preparation.
4. Indications of the order in which medications were added during product preparation.
5. Prescriber's order including patient name, drug name, dose, route of administration, schedule of drug administration, reason for administration, and signature of the prescriber or his agent.
6. Documentation that includes drug name, strength, lot number, expiration date, date, time, number of units to be removed from the pharmacy, worker initials, worker signature and title.
7. Auxiliary labels.
8. Special storage requirements for medication.
9. Drug information references.

Please note that the above list is only exemplary and that the actual items and/or the number of items included in captured images may vary from embodiment to embodiment. The pharmacist may review the captured image(s) on computer 300 to verify that the nurse recorded proper documentation for record keeping purposes, according to one embodiment.

When remotely supervising and/or verifying pharmacy work performed at institutional pharmacy 120, a pharmacist at remote pharmacist site 110 may download one or more captured images from system website 130. Alternatively, captured images may be directly transmitted from institutional pharmacy 120 to remote pharmacist site 110, as described above. The pharmacist may review the medication order entry shown on the image of the patient's Medication Administration Record in one of the captured images. He may also compare it to an image showing the actual pharmacy work performed, and may verify that an order number on the Medication Administration Record matches an order number listed on the sterile intravenous product label also shown in the captured image. The pharmacist may further inspect the captured image(s) to observe one or more of the following:

1. The label on the intravenous product is complete and correct according to the medication order, properly lists the base solution used, and has been initialed by the nurse.
2. The nurse added the correct diluent and the correct and accurate volume to reconstitute the medication vial.
3. The correct medication vial was selected for reconstitution, and that the correct and accurate volume of the reconstituted medication solution was added to the final product.
4. The intravenous product has a sterile seal on the port designed for addition of medication.
5. There is no obvious particulate matter in the solution, as seen in the image.

Please note that the above list is exemplary and that the actual steps taken by a pharmacist when remotely supervising and/or verify pharmacy functions may vary from embodiment to embodiment.

The pharmacist may also indicate that the work has been supervised and/or verified according to the captured images, and is authorized for removal from the pharmacy or to be placed into regular pharmacy stock, according to one embodiment. A pharmacist may indicate that pharmacy work has been verified in any of a number of different ways, according to various embodiments. For example, in one embodiment, a pharmacist may graphically insert a notation into one or more of the images as an indication that the work displayed in the images has been supervised and/or verified. Alternatively, a pharmacist may electronically initial one or more of the captured images. In another embodiment, the verifying pharmacist may create a document referencing the captured images and a relevant pharmacy or medication order and indication that the corresponding pharmacy work was been verified according to the captured images. Such a document may be transmitted to the institutional pharmacy or may be uploaded to and stored on system website 130, according to various embodiments.

Additionally, an electronic record or a hard copy of the verified captured image(s) may be stored at the remote pharmacist site, and/or at system website 130. In yet another example, a pharmacist may utilize digital signature technology to digitally sign one or more of the captured images or another document indicating pharmacist verification of the pharmacy work performed according to the captured images. In another embodiment, an indication that the pharmacist verified the pharmacy work according to the captured images may be transmitted to institutional pharmacy 120, either directly or indirectly. For example, a document including such an indication may be emailed or faxed to institutional pharmacy 120.

The pharmacist at a remote pharmacist site may also transmit the electronically notated image(s), or a copy thereof, from remote pharmacist site 110 to institutional pharmacy site 120 via an Internet connection, virtual private network, or any wired or wireless link, in one embodiment. This may be done to communicate to non-pharmacist personnel that the work passed supervision, is verified, and is authorized for removal from the pharmacy or to be placed into regular pharmacy stock, according to some embodiments. The image may be further notated at the institutional pharmacy 120 and an electronic or hard copy record of the supervised and verified image may be stored at institutional pharmacy 120.

Additionally, at remote pharmacist site 110, the supervised, verified, and pharmacist-initialed captured images, or other document(s) indicating that the pharmacy work was correctly verified, may be printed, such as on printer 330 and/or transmitted to institutional pharmacy 120 via facsimile or other method, such as email. The facsimile may be received in the pharmacy at institutional pharmacy 120. A nurse or other personnel may review the verified documents and verify that it has the pharmacist's initials, which may authorize her to remove the medication from the pharmacy, according to some embodiments. She may write a removal time on the papers and store them in an appropriate place so the next pharmacist on duty at the facility may review and/or file the papers for the pharmacy's records.

If, during the supervision and verification process, a pharmacist at remote pharmacist site 110 discovers, through inspection of the captured images, errors in the work performed by the non-pharmacist, the pharmacist may notify both the non-pharmacist who performed the work, as well as other supervisory personnel, about the errors so that corrective measures may be taken, according to some embodiments.

Figure 6:
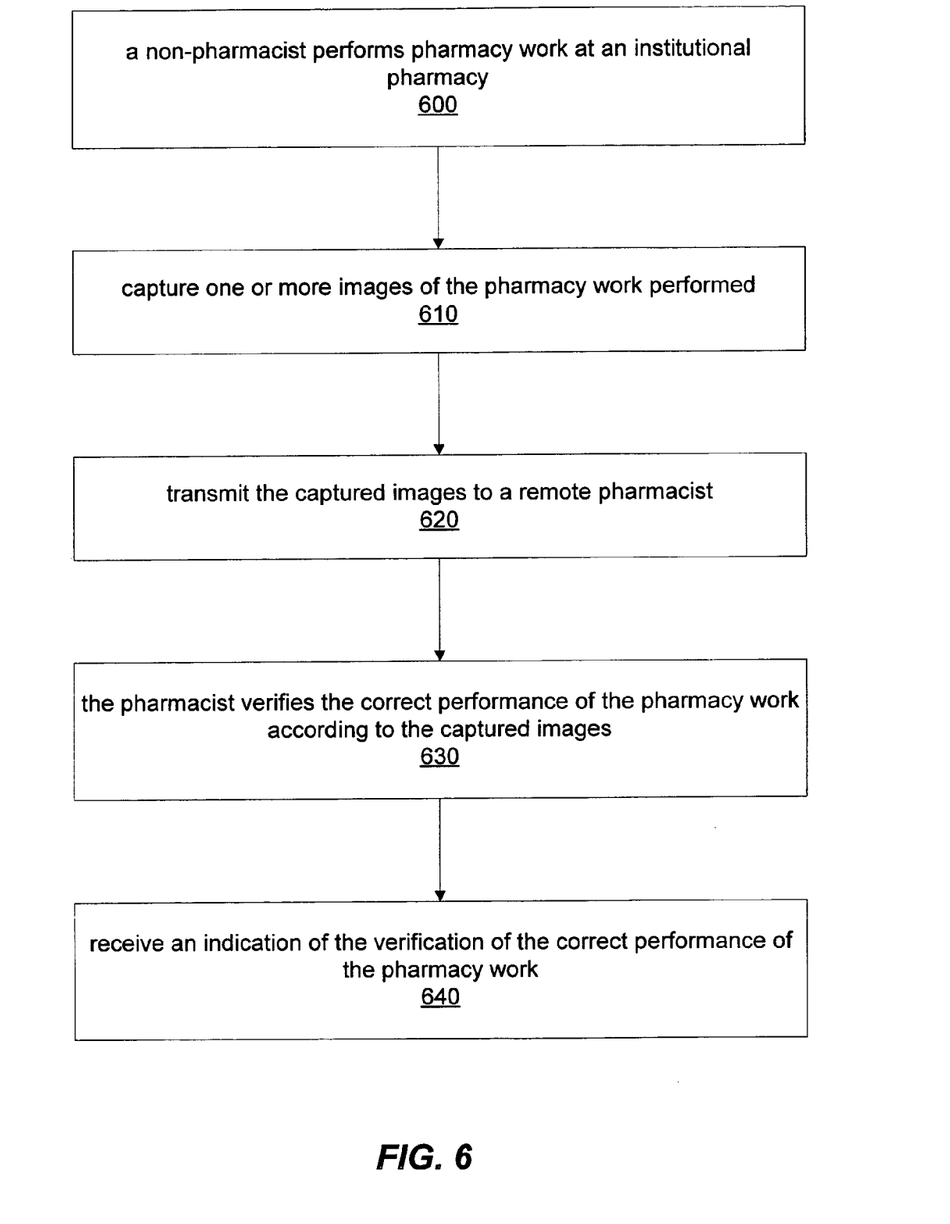
FIG. 6 is a flowchart illustrating a method for remotely supervising and verifying pharmacy functions, according to one embodiment.

FIG. 6 illustrates one embodiment of a method for remotely supervising and verifying pharmacy work performed by a non-pharmacist. As described above, a non-pharmacist may perform pharmacy work at an institutional pharmacy for a pharmacy work task requiring pharmacist supervision, verification or both, as illustrated by block 600. For instance, an institution, such as a hospital or correctional facility, may not have a pharmacist on duty all the time and a patient may require medication that can only be obtained through the institution's pharmacy. Thus, a non-pharmacist, such as a nurse or pharmacy technician, may perform the pharmacy functions required to fulfill the order. Pharmacy functions that may be remotely supervised and verified include, but are not limited to, medication preparation, packaging, prepackaging, compounding, and/or labeling of either single unit packages, multiple dose packages, in batches or in bulk. The non-pharmacist may capture one or more images of the pharmacy work, as illustrated by block 610. Images of pharmacy work may be captured at various times during the performance of the pharmacy work, in some embodiments. In other embodiments, images may be captured of the finished medication product and all materials and documentation required for the performing the pharmacy work, as described herein above.

The captured images may be transmitted to a remote pharmacist, as illustrated by block 620. Thus, as described above, the captured images may be sent to a remote pharmacist for remote supervision and review, as described above. For example, the images may be sent directly to the remote pharmacist via email, in one embodiment. In other embodiments, the captured images may be uploaded to a website from which the remote pharmacist may download them. Additionally, other documentation may also be sent to the pharmacist either by email, uploading to a website, via fax, or by any suitable means. After receiving the captured images, the remote pharmacist may verify the correct performance of the pharmacy work according to the captured images, as illustrated by block 630. For instance, the pharmacist may examine the captured images and other documents to ensure that the correct ingredients, materials, and measures were used when performing the various pharmacy functions. If the pharmacist is able to conduct process checks and verify that the pharmacy work was correctly performed, she may indicate such by initialing or digitally signing one or more of the captured images, according to one embodiment. In other embodiments, the pharmacist may indicate the verification that the pharmacy work was correctly performed according to the captured images by creating a separate verification document or record. The pharmacist may send such verification to the institutional pharmacy.

The institutional pharmacy may receive an indication of the verification of the correct performance of the pharmacy work, as illustrated by block 640. For instance, the pharmacist may email an indication that the pharmacy work was verified, or alternatively, may upload such an indication to system website 130 from which the institutional pharmacy may download it, according to different embodiments. Alternatively, in another embodiment, the pharmacist may fax such an indication to the institutional pharmacy. After receiving an indication that the remote pharmacist verified the pharmacy work, the medication or other pharmacy product produced by the pharmacy work may be further processed or removed from the pharmacy.

Figure 7:
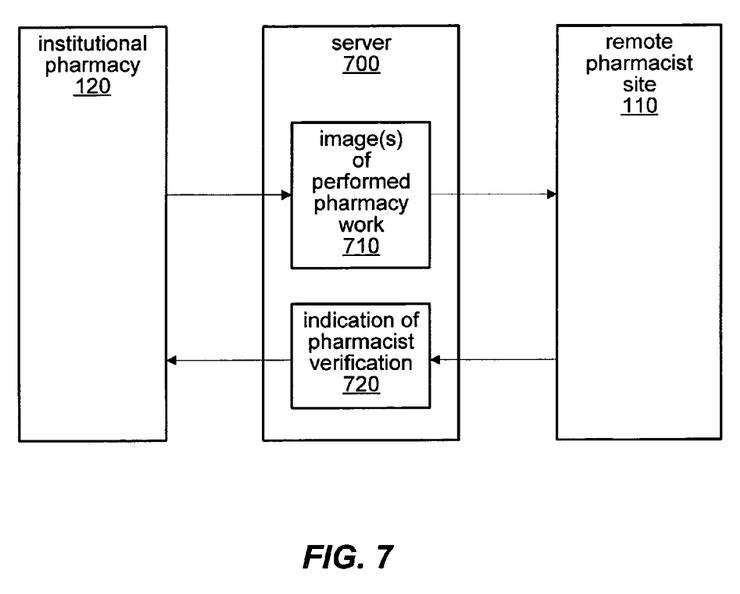
FIG. 7 is a block diagram illustrating a server facilitating remote supervision and verification of pharmacy functions, in one embodiment.

As noted above, in some embodiments, a remote pharmacist may remotely supervise and verify pharmacy functions according to images of the performed pharmacy work that transmitted directly between an institutional pharmacy and the remote pharmacist. In other embodiments, however, institutional pharmacies and remote pharmacists may use a network addressable server, such as may be part of system website 130, to communicate and transfer images and/or other data or documents related to remotely verifying pharmacy functions. FIG. 7 is a block diagram illustrating the use of server 700 by institutional pharmacy 120 and remote pharmacist site 110 for communication and data (image) exchange as part of remote verification of pharmacy functions. Server 700 may be located at institutional pharmacy 120, remote pharmacist site 110, or at a location separate from either institutional pharmacy 120 or remote pharmacist site 110, according to various embodiments. Server 700 may be addressable via network 100, which in some embodiments, may be the Internet. In other embodiments, however, server 700 may be accessible via other methods, such as via a corporate LAN/WAN, direct modem communication, or other wired or wireless technology. In some embodiments, server 700 may be a web server, while, in other embodiments, server 700 may be a bulletin board system allowing posts and retrieval of images and/or other documents. Server 700 may provide security, such as requiring user names and passwords, or other user authentication, to prevent unauthorized accessing of pharmacy related images or information. In general, server 700 may utilize any of numerous data and communication security techniques, such as encryption, user authentication, HTTPS communication, etc.

When utilizing a server, such as server 700, for communication related to remote verification of pharmacy functions, the non-pharmacist performing the pharmacy work may upload or transmit one or more images of performed pharmacy work (or, alternatively, images of the work as it is being performed), to server 700. For example, in one embodiment, images may be transmitted via FTP or another network file transfer protocol. Server 700 may then store the received images for later access by a remote pharmacist. In some embodiments, the images may be associated with a job or task identifier that may be used by a pharmacist to reference the images for review.

Server 700 may also provide an interface for review of images by pharmacists, according to some embodiments. For instance, server 700 may notify the pharmacist that the images have been stored and are available for review. Server 700 may also allow the pharmacist to download or otherwise retrieve the images from server 700 for review locally on the pharmacist's computer. Alternatively, in another embodiment, server 700 may provide an interface for online reviewing of images. For example, server 700 may generate web pages allowing a pharmacist to view the stored images of performed pharmacy work with a standard web browser program without having to retrieve or save the images locally.

After reviewing the images to verify whether the pharmacy work was performed correctly, a pharmacist may upload to server 700 an indication of the verification, according to the images, of the pharmacy work performed. For example, in one embodiment, the pharmacist may upload a copy of one or more of the images to which the pharmacist's digital signature is attached as an indication of the verification of the pharmacy work. In another embodiment, however, the pharmacist may upload a separate document including an indication of his verification of the pharmacy work. In yet another embodiment, server 700 may provide an interface, such as via generated web pages, allowing a pharmacist to record on server 700 an indication of the verification of the pharmacy work according to the images.

Server 700 also may, in some embodiments, notify the non-pharmacist that the pharmacist has recorded or uploaded an indication of the verification of the pharmacy work. Thus, server 700 may direct the communication between the non-pharmacist at the institutional pharmacy and the remote pharmacist. Additionally, server 700 may provide an interface for the institutional pharmacy to access, view, and/or download the pharmacist's indication that the pharmacy work was verified. Server 700 may provide an interface allowing the non-pharmacist or institutional pharmacy to download whatever data or documents were stored on server 700 by the pharmacist, according to one embodiment. Alternatively, server 700 may allow personnel at the institutional pharmacy to view data and/or documents from the remote pharmacist site online without having to download and store them locally at the institutional pharmacy. For example, in one embodiment, server 700 may generate web pages allowing review of data and/or documents stored on server 700 by a remote pharmacist.

Using a server, or other shared storage area, for communication between an institutional pharmacy and a remote pharmacist may also facilitate review and/or supervision of the remote verification process by administrators or others. For instance, server 700 may provide an interface allowing a director of an institutional pharmacy to access, examine and/or review the images from the institutional pharmacy as well as any data or documents from remote pharmacists. Additionally, server 700 may be configured to work in conjunction with other software on workstations at institutional pharmacies and/or remote pharmacist sites. For example, custom software, such as remote verification software 140, configured specifically for communication and data exchange as part of remote verification of pharmacy functions may provide a user interface for uploading, downloading, and/or reviewing images stored on server 700, according to one embodiment.

Figure 8:
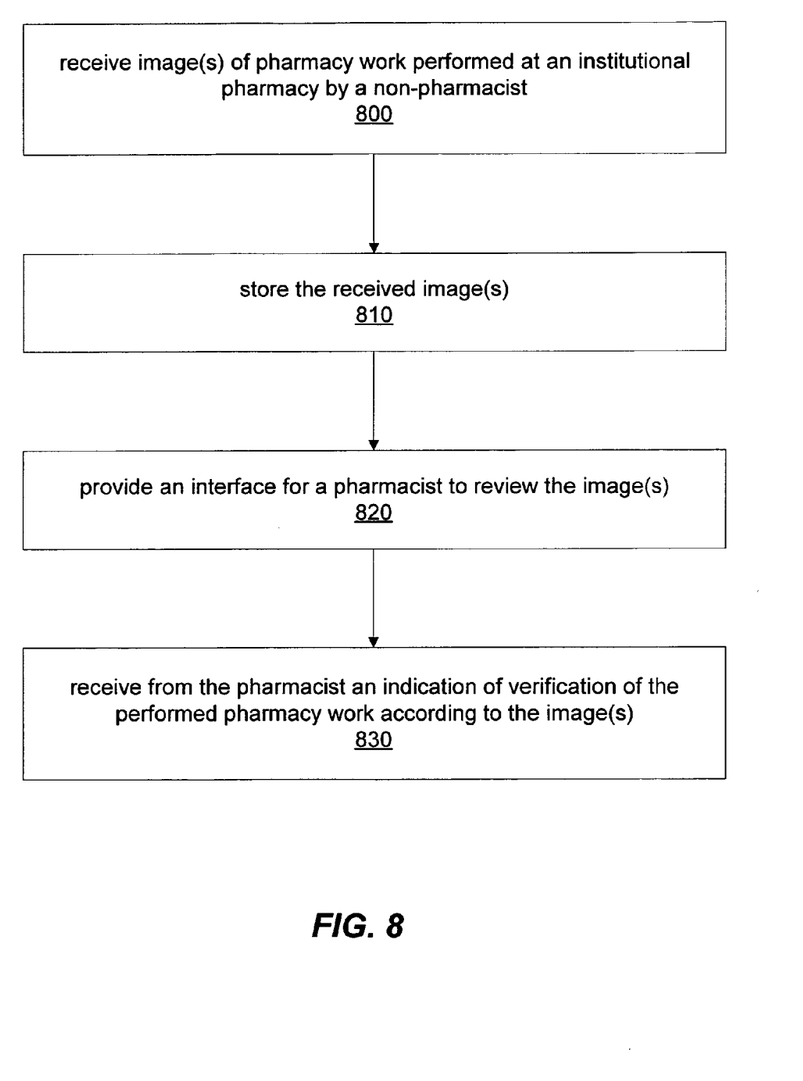
FIG. 8 is flowchart illustrating one embodiment of a method for utilizing a network accessible server for remote supervision and verification of pharmacy functions.

FIG. 8 illustrates a flowchart for one embodiment of a method for a server, such as server 700 described above, to facilitate remote supervision of pharmacy functions, as described herein. For instance, server 700 may receive one or more images of pharmacy work performed by a non-pharmacist at an institutional pharmacy, such as institutional pharmacy 120, as illustrated by block 800. As noted above, images of performed pharmacy work maybe uploaded, posted, or otherwise transmitted to server 700. Server 700 may store the received images for later access, retrieval, and/or review, as illustrated by block 810. Server 700 may store received images in any of variety of manners and formats, according to various embodiments. Images may be stored as individual files on a file server, as records in an image database, or multiple images may be compacted and stored together in a single file, such as in a .ZIP file, in some embodiments.

Server 700 may also provide an interface for a remote pharmacist, such as one at remote pharmacist site 110, to review the images, as illustrated by block 820. For example, in one embodiment, server 700 may provide a web interface, consisting of one or more generated web pages, allowing a remote pharmacist to review images using a standard web browser program. In another embodiment, server 700 may implement a messaging interface allowing custom software for remote verification of pharmacy functions, such as remote verification software 140, to send messages requesting the storage or retrieval of images, documents or other data. In general, server 700 may allow a remote pharmacist to access the images stored on server 700 by an institutional pharmacy.

After reviewing the pharmacy work according to the images, a pharmacist may record or store on server 700 an indication of his verification of the pharmacy work. Thus, server 700 may receive from the pharmacist an indication of verification of the performed pharmacy work according to the images, as illustrated by block 830. In some embodiments, server 700 may provide an interface allowing the pharmacist to record such an indication. In another embodiments, the pharmacist may upload a document or image including such an indication. For example, the pharmacist may attach a digital signature or other digital certificate to one or more of the images and upload the image(s) to server 700 and the institutional pharmacy may be able to download or otherwise access the pharmacist's indication. Alternatively, the pharmacist may generate and store a separate document including an indication of the verification of the performed pharmacy work. In some embodiments, such a document may include details of the verification or may include issues or problems discovered in the performance of the pharmacy functions.

Server 700 may, in some embodiments, notify an institutional pharmacy, such as via email or instant messenger, that the pharmacist has finished reviewing the stored images and has recorded an indication of his verification of the pharmacy function according to the images. Additionally, server 700 may implement or provide an interface allowing an institutional pharmacy to access and/or review results of the pharmacist's verification. For example, in one embodiment, server 700 may allow custom software, such as remote verification software 140 to access and/or download the data or documents stored by a remote pharmacist. Alternatively, server 700 may implement a web page based interface allowing an institutional pharmacy to review data and/or documents stored on server 700 by a remote pharmacist.

Figure 9:
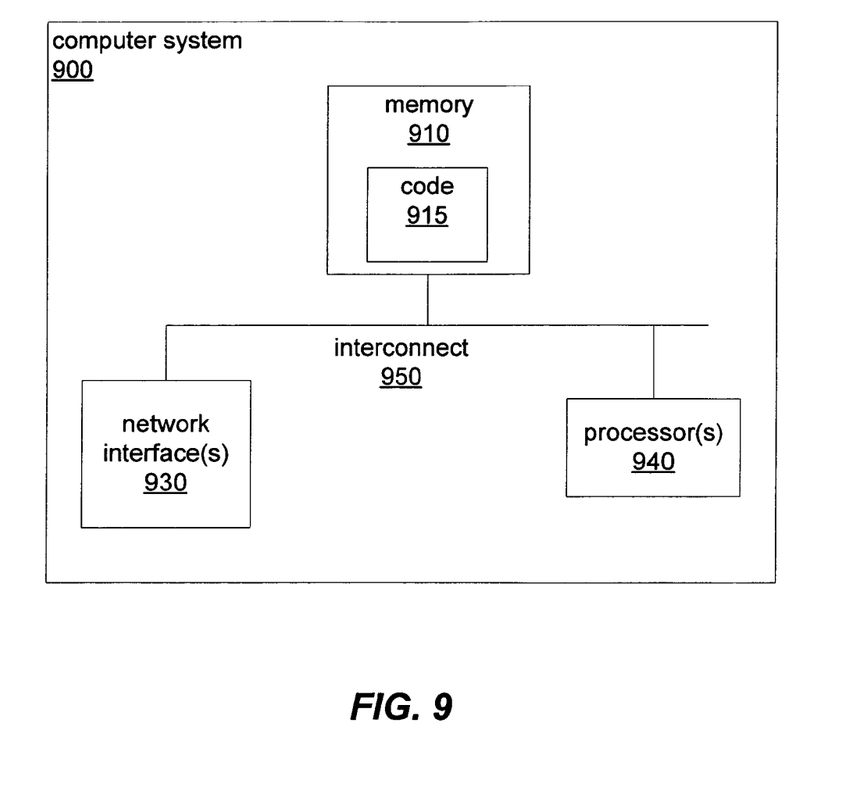
FIG. 9 is a block diagram illustrating an exemplary computer system suitable for implementing remote supervision and verification of pharmacy functions, according to one embodiment.

FIG. 9 is a block diagram illustrating an embodiment of a computer system usable to implement remote pharmacy supervision and verification. In some embodiments, a workstation at either institutional pharmacy 120, remote pharmacist site 110, system website 130, and/or server 700, may include a general-purpose computer system that includes or is configured to access one or more computer-accessible media, such as computer system 900 illustrated in FIG. 9. In the illustrated embodiment, computer system 900 includes one or more processors 940 coupled to a system memory 910 via an interconnect 950. Computer system 900 may further includes a network interface 930 also coupled to interconnect 950.

In various embodiments, computer system 900 may be a uniprocessor system including one processor 940, or a multiprocessor system including several processors 940 (e.g., two, four, eight, or another suitable number). Processors 940 may be any suitable processors capable of executing instructions. For example, in various embodiments, processors 940 may be general-purpose or embedded processors implementing any of a variety of instruction set architectures (ISAs), such as the x86, PowerPC, SPARC, or MIPS ISAs, or any other suitable ISA. In multiprocessor systems, each of processors 940 may commonly, but not necessarily, implement the same ISA.

System memory 910 may be configured to store instructions and data accessible by processor 940. In various embodiments, system memory 910 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those methods and techniques described above for remotely supervising and verifying pharmacy functions, may be stored within system memory 910 as code 915.

In one embodiment, interconnect 950 may be configured to coordinate I/O traffic between processor 940, system memory 910, and any peripheral devices in the device, including network interface 930 or other peripheral interfaces. In some embodiments, interconnect 950 may perform any necessary protocol, timing or other data transformations to convert data signals from one component (e.g., system memory 910) into a format suitable for use by another component (e.g., processor 940). In some embodiments, interconnect 950 may include support for devices attached through various types of peripheral buses, such as a variant of the Peripheral Component Interconnect (PCI) bus standard or the Universal Serial Bus (USB) standard, for example. In some embodiments, the function of interconnect 950 may be split into two or more separate components, such as a north bridge and a south bridge, for example. Also, in some embodiments some or all of the functionality of interconnect 950, such as an interface to system memory 910, may be incorporated directly into processor 940.

Network interface 930 may be configured to allow data to be exchanged between computer system 900 and other devices attached to a network, such as other computer systems, for example. Network interface 930 may commonly support one or more wireless networking protocols (e.g., Wi-Fi/IEEE 802.11, or another wireless networking standard). However, in various embodiments, network interface 930 may support communication via any suitable wired or wireless general data networks, such as other types of Ethernet network, for example. Additionally, network interface 930 may support communication via telecommunications/telephony networks such as analog voice networks or digital fiber communications networks, via storage area networks such as Fibre Channel SANs, or via any other suitable type of network and/or protocol.

In some embodiments, system memory 910 may be one embodiment of a computer-accessible medium configured to store program instructions and data as described above. However, in other embodiments, program instructions and/or data may be received, sent or stored upon different types of computer-accessible media. Generally speaking, a computer-accessible medium may include storage media or memory media such as magnetic or optical media, e.g., disk or DVD/CD coupled to computer system 1100 via interconnect 950. A computer-accessible medium may also include any volatile or non-volatile media such as RAM (e.g. SDRAM, DDR SDRAM, RDRAM, SRAM, etc.), ROM, etc, that may be included in some embodiments of computer system 900 as system memory 910 or another type of memory. Further, program instructions or data on a computer-accessible medium may be transmitted via transmission media or signals such as electrical, electromagnetic, or digital signals, conveyed via a communication medium such as a network and/or a wireless link, such as may be implemented via network interface 930.

The various methods as illustrated in the figures and described herein represent exemplary embodiments of methods. The methods may be implemented manually, in software, in hardware, or a combination thereof. The order of any method may be changed, and various elements may be added, reordered, combined, omitted, modified, etc. Additionally, various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A method for remote supervision and verification of pharmacy functions that are performed by a non-pharmacist person, comprising:
    in response to performance, by a non-pharmacist person, of pharmacy work to prepare a medication at an institutional pharmacy, wherein the pharmacy work requires pharmacist verification of the pharmacy work, wherein performing the pharmacy work comprises the non-pharmacist person performing, at a workstation in the institutional pharmacy, a sterile compounding process to prepare the medication, wherein the medication is compounded from a plurality of material components at the workstation within the institutional pharmacy:
    capturing, via an image capture device at the workstation in the institutional pharmacy, one or more images of the pharmacy work performed by the non-pharmacist person as the work is performed by the non-pharmacist person at the institutional pharmacy, wherein at least one of the images is an image of the sterile compounding process performed by the non-pharmacist person that requires verification by a pharmacist for medications to be placed into pharmacy stock;
    implementing verification software, via one or more computers at the institutional pharmacy, to remotely verify the work performed by the non-pharmacist person, wherein remote verification of the work performed by the non-pharmacist person comprises:
    transmitting the one or more images captured by the image capture device of the sterile compounding process performed by the non-pharmacist person at the workstation to a remote pharmacist for review, wherein said transmitting the one or more images comprises storing the images on a website; receiving an indication of the remote pharmacist's verification of the correct performance of the sterile compounding process by the non-pharmacist person; and
    providing, in response to the indication of the remote pharmacist's verification, an indication at the institutional pharmacy that the remote pharmacist has verified the sterile compounding process performed by the non-pharmacist person.

2. The method of claim 1, wherein the one or more captured images include one or more images of a plurality of material components for performing the pharmacy work and one or more measures for the material components.

3. The method of claim 1, wherein the one or more captured images include one or more still images or one or more video clips.

4. The method of claim 1, wherein said transmitting the one or more images comprises transmitting the one or more images via a real-time collaboration tool.

5. The method of claim 1, further comprising the pharmacist accessing the still images from the website.

6. The method of claim 1, wherein said receiving an indication comprises: storing the indication of the pharmacist's verification of the correct performance of the sterile compounding process on the website; and the non-pharmacist accessing the indication of the pharmacist's verification on the website.

7. The method of claim 1, further comprising transmitting one or more documents related to the performed pharmacy work to the remote pharmacist.

8. The method of claim 1, wherein the pharmacy work is performed pursuant to a medication order; and wherein each of the one or more images comprises an indication of the medication order.

9. The method of claim 1, further comprising performing, via one or more computers at the institutional pharmacy:
    receiving an indication of the remote pharmacist's authorization for the sterile compounded medications; and
    providing an indication at the institutional pharmacy site that the remote pharmacist has authorized the sterile compounded medications.

10. The method of claim 9, further comprising placing the sterile compounded medications into regular pharmacy stock at the institutional pharmacy after receiving authorization from the remote pharmacist.

11. The method of claim 1, wherein the remote pharmacist remotely verifies, via a computer, pharmacy functions performed at the institutional pharmacy and at one or more additional institutional pharmacies.

12. The method of claim 1, wherein the remote pharmacist remotely verifies, via a computer, pharmacy functions performed at the institutional pharmacy and at one or more additional institutional pharmacies, wherein the remote pharmacist accesses the orders through at least one pharmacy order entry system for at least one of the institutional pharmacies, wherein the pharmacist remotely verifies pharmacy functions at the institutional pharmacy and at one or more additional institutional pharmacies on a first-come, first-served basis in which the institutional pharmacies are serviced in the order they notified the remote pharmacist that images were available for verification.

13. The method of claim 1, wherein capturing the one or more images comprises capturing two or more images of the sterile compounding process of the sterile compounded medications as the sterile compounded medications are prepared, wherein at least one of the two or more images is captured at a different stage of the compounding of the sterile compounded medications than at least one other of the two or more images.

14. The method of claim 13, wherein at least two of the two more images captured by the image capture device at the workstation are uploaded as a single post for a remote pharmacist for review.

15. The method of claim 13, wherein, for each of at least two steps in the sterile compounding process of the sterile compounded medications, the remote pharmacist provides to the institutional pharmacy, on a step-by-step basis, a verification of the step using at least one captured image for the step.

16. A method for remote supervision and verification of pharmacy functions that are performed by a non-pharmacist person, comprising:
    in response to performance, by a non-pharmacist person, of pharmacy work to prepare a medication at an institutional pharmacy, wherein the pharmacy work requires pharmacist verification of the pharmacy work, wherein performing the pharmacy work comprises the non-pharmacist person performing, at a workstation in the institutional pharmacy, a sterile compounding process to prepare the medication, wherein the medication is compounded from a plurality of material components at the workstation within the institutional pharmacy:
        capturing, via an image capture device at the workstation in the institutional pharmacy, one or more images of the pharmacy work performed by the non-pharmacist person as the work is performed by the non-pharmacist person at the institutional pharmacy, wherein at least one of the images is an image of the sterile compounding process performed by the non-pharmacist person that requires verification by a pharmacist for medications to be placed into pharmacy stock;
        wherein capturing the one or more images comprises capturing two or more images of the sterile compounding process of the sterile compounded medications as the sterile compounded medications are prepared, wherein at least one of the two or more images is captured at a different stage of the compounding of the sterile compounded medications than at least one other of the two or more images;
        implementing verification software, via one or more computers at the institutional pharmacy, to remotely verify the work performed by the non-pharmacist person, wherein remote verification of the work performed by the non-pharmacist person comprises:
            transmitting the one or more images captured by the image capture device of the sterile compounding process performed by the non-pharmacist person at the workstation to a remote pharmacist for review;
            receiving an indication of the remote pharmacist's verification of the correct performance of the sterile compounding process by the non-pharmacist person; and
            providing, in response to the indication of the remote pharmacist's verification, an indication at the institutional pharmacy that the remote pharmacist has verified the sterile compounding process performed by the non-pharmacist person.

17. The method of claim 16, wherein the one or more captured images include one or more images of a plurality of material components for performing the pharmacy work and one or more measures for the material components.

18. The method of claim 16, wherein the one or more captured images include one or more still images or one or more video clips.

19. The method of claim 16, wherein said transmitting the one or more images comprises transmitting the one or more images via email or via a real-time collaboration tool.

20. The method of claim 16, further comprising transmitting one or more documents related to the performed pharmacy work to the remote pharmacist.

21. The method of claim 16, wherein the pharmacy work is performed pursuant to a medication order; and wherein each of the one or more images comprises an indication of the medication order.

22. The method of claim 16, further comprising performing, via one or more computers at the institutional pharmacy:
    receiving an indication of the remote pharmacist's authorization for the sterile compounded medications; and
    providing an indication at the institutional pharmacy site that the remote pharmacist has authorized the sterile compounded medications.

23. The method of claim 22, further comprising placing the sterile compounded medications into regular pharmacy stock at the institutional pharmacy after receiving authorization from the remote pharmacist.

24. The method of claim 16, wherein the remote pharmacist remotely verifies, via a computer, pharmacy functions performed at the institutional pharmacy and at one or more additional institutional pharmacies.

25. The method of claim 16, wherein the remote pharmacist remotely verifies, via a computer, pharmacy functions performed at the institutional pharmacy and at one or more additional institutional pharmacies, wherein the remote pharmacist accesses the orders through at least one pharmacy order entry system for at least one of the institutional pharmacies, wherein the pharmacist remotely verifies pharmacy functions at the institutional pharmacy and at one or more additional institutional pharmacies on a first-come, first-served basis in which the institutional pharmacies are serviced in the order they notified the remote pharmacist that images were available for verification.

26. The method of claim 16, wherein at least two of the two more images captured by the image capture device at the workstation are uploaded as a single post for a remote pharmacist for review.

27. The method of claim 16, wherein, for each of at least two steps in the sterile compounding process of the sterile compounded medications, the remote pharmacist provides to the institutional pharmacy, on a step-by-step basis, a verification of the step using at least one captured image for the step.

* * * * *